United States Patent
Abe et al.

(10) Patent No.: US 10,160,952 B2
(45) Date of Patent: Dec. 25, 2018

(54) METHOD FOR MANUFACTURING AN IMMUNE CELL-CONTAINING COMPOSITION, AND A CANCER-TREATING COMPOSITION

(71) Applicants: Hiroyuki Abe, Fuchu (JP); Seiichi Yusa, Tokyo (JP)

(72) Inventors: Hiroyuki Abe, Fuchu (JP); Seiichi Yusa, Tokyo (JP)

( * ) Notice: Subject to any disclaimer, the term of this patent is extended or adjusted under 35 U.S.C. 154(b) by 0 days.

(21) Appl. No.: 14/760,906

(22) PCT Filed: Jan. 14, 2014

(86) PCT No.: PCT/JP2014/050484
§ 371 (c)(1),
(2) Date: Jul. 14, 2015

(87) PCT Pub. No.: WO2014/112491
PCT Pub. Date: Jul. 24, 2014

(65) Prior Publication Data
US 2016/0024471 A1    Jan. 28, 2016

(30) Foreign Application Priority Data

Jan. 15, 2013 (JP) ................................. 2013-004495

(51) Int. Cl.
| | | |
|---|---|---|
| C12N 5/0783 | (2010.01) | |
| A61K 35/12 | (2015.01) | |
| A61K 35/15 | (2015.01) | |
| A61K 35/17 | (2015.01) | |

(52) U.S. Cl.
CPC ............ *C12N 5/0638* (2013.01); *A61K 35/15* (2013.01); *A61K 35/17* (2013.01); *C12N 5/0646* (2013.01); *A61K 2035/124* (2013.01); *C12N 2501/2302* (2013.01); *C12N 2501/2315* (2013.01); *C12N 2501/599* (2013.01); *C12N 2501/998* (2013.01); *C12N 2506/11* (2013.01)

(58) Field of Classification Search
CPC ................ C12N 5/0638; C12N 5/0646; C12N 2501/998; C12N 2506/11; C12N 2501/599; C12N 2501/2315; C12N 2501/2302; A61K 35/17; A61K 35/15; A61K 2035/124
See application file for complete search history.

(56) References Cited

U.S. PATENT DOCUMENTS

| | | | |
|---|---|---|---|
| 2012/0171173 A1 | 7/2012 | Ideno et al. | |
| 2012/0308986 A1* | 12/2012 | Deng | C12N 5/0646 435/2 |
| 2013/0157364 A1 | 6/2013 | Hong et al. | |

FOREIGN PATENT DOCUMENTS

| | | |
|---|---|---|
| CN | 102597223 A | 7/2012 |
| EP | 2535052 A1 | 12/2012 |
| EP | 2537923 A1 | 12/2012 |
| JP | 2007297291 A | 11/2007 |
| JP | 2011529341 A | 12/2011 |
| JP | 2013071915 A | 4/2013 |
| JP | 2013081428 A | 5/2013 |
| JP | 2014030375 A | 2/2014 |
| WO | 2004056392 A1 | 7/2004 |
| WO | 2011030851 A1 | 3/2011 |
| WO | 2012030057 A2 | 3/2012 |

OTHER PUBLICATIONS

International Search Report corresponding to Application No. PCT/JP2014/050484; dated Apr. 15, 2014, with English translation.
De Rham, Casimir et al: "The proinflammatory cytokines IL-2, IL-15 and IL-21 modulate the repertoire of mature human natural killer cell receptors", Arthritis Research and Therapy, Biomed Central, London, GB, vol. 9, No. 6, Dec. 3, 2007 p. R125.
Extended European Search Report for European Patent Application No. 14740451.1-1402/2947144 PCT/JP2014/059484; dated May 10, 2016.

* cited by examiner

*Primary Examiner* — Taeyoon Kim
(74) *Attorney, Agent, or Firm* — Cantor Colburn LLP

(57) ABSTRACT

To provide a method in which mononuclear cells are differentiated into a good balance of NK cells, NKT cells, and T cells, and said cells are made to proliferate. The present invention provides a method for manufacturing an immune cell-containing composition, said method including the following steps: a first step in which mononuclear cells are cultured in a medium containing anti-CD16 monoclonal antibodies and either IL-2 and/or IL-15; and a second step, after the first step, in which culturing is performed under conditions that make the mononuclear cells preferentially differentiate into cytotoxic T cells. This method may also include a third step, after the second step, in which culturing is performed in a medium containing anti-CD16 monoclonal antibodies and either IL-2 and/or IL-15.

4 Claims, 5 Drawing Sheets

FIG. 4
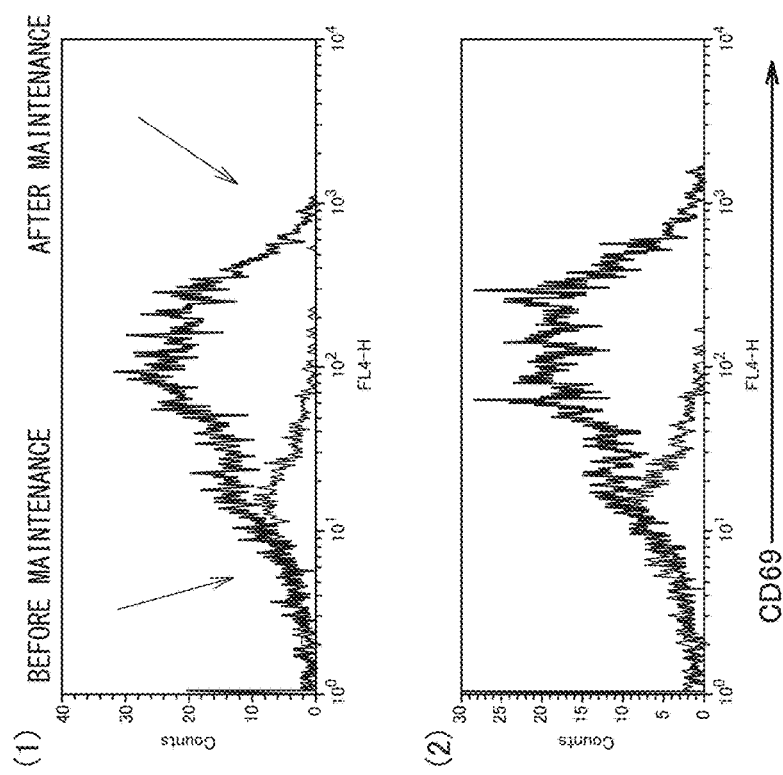
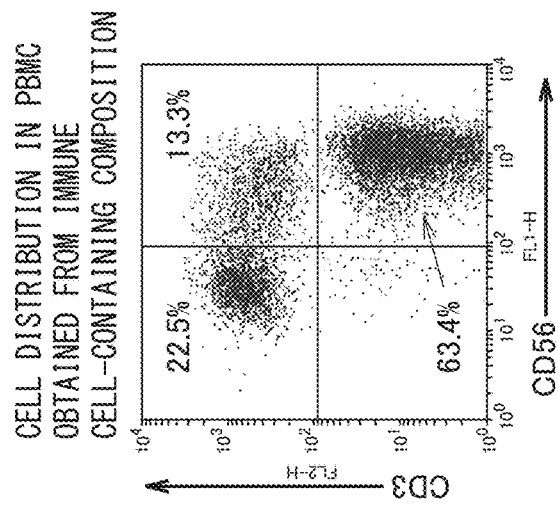

METHOD FOR MANUFACTURING AN IMMUNE CELL-CONTAINING COMPOSITION, AND A CANCER-TREATING COMPOSITION

TECHNICAL FIELD

The present invention relates to a method of manufacturing an immune cell-containing composition and a composition for treating cancer.

BACKGROUND ART

In recent years, various methods for treating cancer have been developed. In particular, immunotherapy, which can enhance patient's immunocompetence, has gathered attention. Examples of immunotherapy include, for example, cellular immunotherapy and the like.

Cellular immunotherapy, which is also referred to as adoptive immunotherapy and the like, is intended for enhancing patient's immunocompetence by activating and proliferating immune cells from the patient in vitro and then returning the cells to that patient. For example, the LAK therapy, which is one example of cellular immunotherapy, involves separating mononuclear cells from a blood sample withdrawn from a patient, and allowing the resulting mononuclear cells to differentiate mainly into cytotoxic T cells and the like and then returning the cytotoxic T cells and the like into the patient's body. Further, a method in which cells such as NK cells are used has been known as another cellular immunotherapy (for example, see Patent Document 1).

Patent Document 1: Japanese Unexamined Patent Application (Translation of PCT Application), Publication No. 2011-529341

DISCLOSURE OF THE INVENTION

Problems to be Solved by the Invention

Meanwhile, the present inventors find that immunocompetence in vivo may not be necessarily enhanced even when mononuclear cells are allowed to differentiate into a single type of immune cell, such as cytotoxic T cells, and a cultured material (a culture) obtained by proliferating the resulting immune cells is returned into the body as in conventional cellular immunotherapy. Therefore, an object of the present invention is to differentiate mononuclear cells into multiple types of immune cells (in particular, NK cells, NKT cells and T cells) in a well-balanced manner and to proliferate these cells.

Means for Solving the Problems

The present inventors find that the above object can be achieved by combining specific cell culture steps in a method of manufacturing immune cells. Then the present invention has been completed. Specifically, the present invention provides the followings.

(1) A method of manufacturing an immune cell-containing composition, the method comprising a first step of culturing mononuclear cells in a culture medium containing IL-2 and/or IL-15 and anti-CD16 monoclonal antibody, and a second step of performing culturing after the first step under conditions where the mononuclear cells are preferentially differentiated into cytotoxic T cells.

(2) The method of manufacturing an immune cell-containing composition according to (1), comprising a third step of performing culturing after the second step in a culture medium containing IL-2 and/or IL-15 and anti-CD16 monoclonal antibody.

(3) A composition for treating cancer comprising an immune cell-containing composition manufactured by the manufacturing method according to (1) or (2).

Effects of the Invention

According to the present invention, provided is a method of differentiating mononuclear cells into NK cells, NKT cells and T cells in a well-balanced manner and proliferating these cells.

BRIEF DESCRIPTION OF THE DRAWINGS

FIG. 1(A) shows the cell counts of PBMC recovered from 6 healthy subjects.

FIG. 4 shows results from the FACS analysis of an immune cell-containing composition obtained in an Example of the present invention.

PREFERRED MODE FOR CARRYING OUT THE INVENTION

Figure 1:
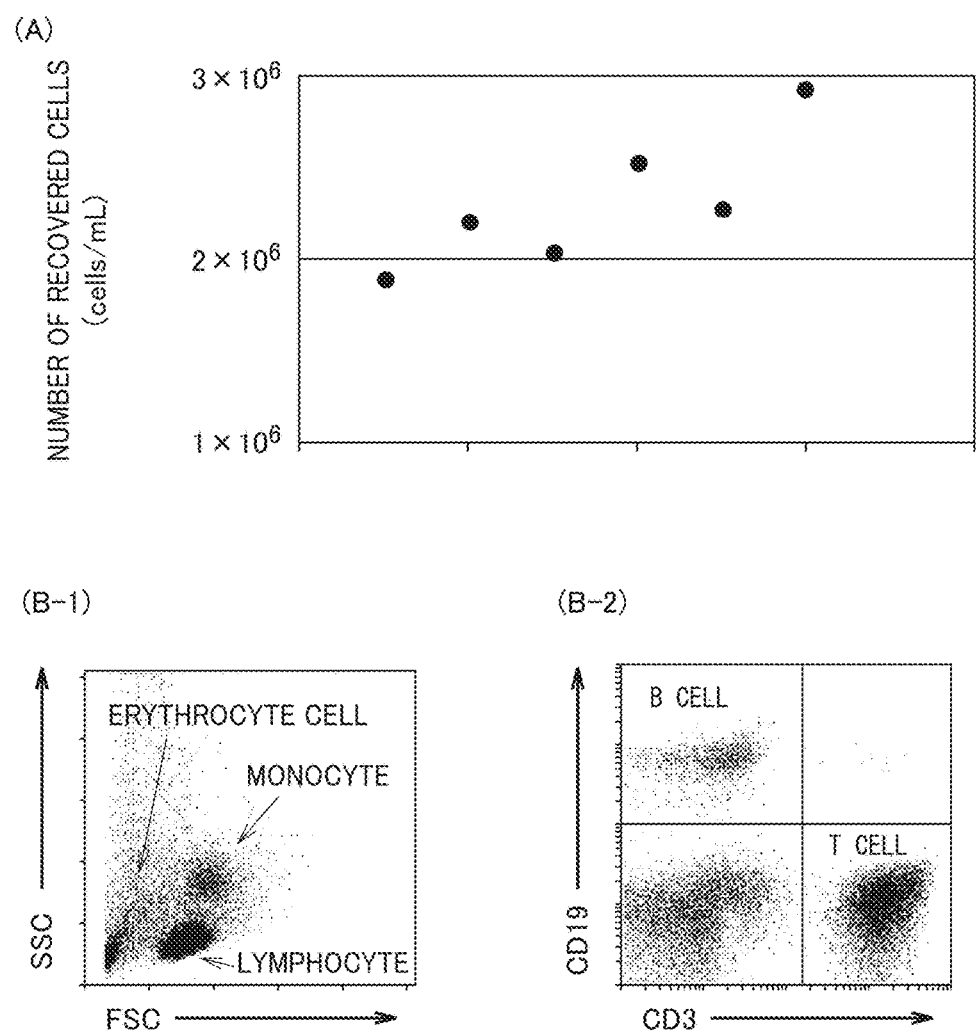
FIGS. 1(B-1) and 1(B-2) show typical results from the FACS analysis of the obtained PBMC.

Below, embodiments of the present invention will be described, but the present invention shall not be limited to these.

The method of manufacturing an immune cell-containing composition according to the present invention comprises a first step and a second step in which culturing is performed under specific conditions. Below, each step will be described. Note that the "immune cell-containing composition" as used in the present invention refers to a composition comprising at least NK cells, NKT cells and T cells.

First Step (Step of Proliferating NK Cells)

The first step in the present invention comprises culturing mononuclear cells in a culture medium described below to differentiate the mononuclear cells into NK cells, NKT cells and the like, and proliferating the NK cells, NKT cells and the like. In this step, mononuclear cells can be selectively differentiated into γδT cells in addition to NK cells and NKT cells, and then they can be amplified. NK cells (natural killer cells), NKT cells (natural killer T cells) and γδT cells, which are each a type of lymphocyte, are known to have a function to attack cancer cells. Note that "NK cells and the like" as used in the present invention refers to at least NK cells and NKT cells.

(Mononuclear Cell)

A mononuclear cell is a general term for a lymphocyte and a monocyte. Mononuclear cells may be obtained from body fluids (blood such as peripheral blood, bone marrow and cord blood, and the like) by a known method such as centrifugation, magnetic beads and flow cytometry. Mononuclear cells may be those derived from stem cells such as iPS cells, ES cells and somatic stem cells. Peripheral blood mononuclear cells (PBMC) and the like can be preferably used as mononuclear cells in the present invention.

A method comprising separating leukocytes in blood using a apheresis system (which is also referred to as "apheresis") is known as a conventional method for withdrawing mononuclear cells required for cellular immunotherapy. However, the system operation cost for apheresis is expensive, and in addition, advanced skills are required for operating the system.

Further, the total cell count of immune cells to be returned into a patient's body is preferably, for example, one billion or more in a case where lymphocytes are used in order to obtain a desired therapeutic effect from cellular immunotherapy. However, the proportion of mononuclear cells present in blood is small. Therefore, apheresis usually needs to be performed multiple times from the same patient with a certain interval in order to acquire a cell number of one billion or more. However, performing apheresis multiple times imposes significant burden on patients in terms of physical strength and time. Further, the number of mononuclear cells withdrawable by apheresis may vary depending on conditions of patient's blood and the like.

In contrast, in the case of the manufacturing method according to the present invention, mononuclear cells can be efficiently differentiated into immune cells, and the immune cells can be allowed to grow. Therefore, a smaller amount of blood is required for obtaining mononuclear cells (for example, 1 to 100 mL, preferably 1 to 50 mL), and one blood collection may be sufficient. Therefore, the present invention can significantly reduce burdens on patient (in terms of cost, time and the like) to obtain mononuclear cells as compared with the traditional methods such as apheresis. Nonetheless, mononuclear cells in the present invention may be obtained by apheresis.

(Culture Medium)

A culture medium used in the first step contains IL-2 (interleukin-2) and/or IL-15 (interleukin 15) and anti-CD16 monoclonal antibody. A culture medium containing IL-2, IL-15 and anti-CD16 monoclonal antibody is preferred in that mononuclear cells can be selectively differentiated into, in particular, NK cells, NKT cells, γδT cells and the like. By using the above culture medium, mononuclear cells can be differentiated to NK cells, NKT cells, γδT cells and the like, and these immune cells can be allowed to proliferate.

There is no particular limitation for the concentration of IL-2 in a culture medium suitable for differentiation of mononuclear cells into NK cells and the like and subsequent proliferation thereof, but it may be 1 to 200000 IU/mL, preferably 100 to 200000 IU/mL, most preferably 1000 to 200000 IU/mL. Further, there is no particular limitation for the concentration of IL-15 in a culture medium suitable for differentiation of mononuclear cells into NK cells and the like and subsequent proliferation thereof, but it may be 1 to 100 ng/mL, preferably 1 to 50 ng/mL, most preferably 1 to 30 ng/mL. Moreover, there is no particular limitation for the concentration of anti-CD16 monoclonal antibody in a culture medium suitable for differentiation of mononuclear cells into NK cells and the like and subsequent proliferation thereof, but it may be 1 to 100000 ng/mL, preferably 10 to 100000 ng/mL, most preferably 100 to 100000 ng/mL. IL-2, IL-15 and anti-CD16 monoclonal antibody can be blended in a culture medium during the first step within the above concentration ranges.

A culture medium used in the present invention may contain a known NK cell stimulant (such as anti-NKp46 antibody), NKT cell stimulant (such as anti-TCRVa24 antibody, anti-TCRVb11 antibody and alpha galactosyl ceramide), γδT cell stimulant (such as anti-TCR γ/δ, antibody and zoledronic acid) and the like in addition to IL-2 and/or IL-15 and anti-CD16 monoclonal antibody. The loading amounts of these components in a culture medium can be appropriately adjusted depending on the amount of cells to be obtained and the like.

A culture medium used in the present invention may contain a nutrient component for enabling culture of mononuclear cells, a pH adjuster and the like. There is no particular limitation for the culture media containing such components, but examples thereof include serum-free synthetic media for lymphocytes (such as KB550 and KB570), AIM-V, DC Medium, DMEM, RPMI-1640, X-VIVO culture medium and the like. Further, there is no particular limitation for the form of a culture medium used in the present invention, but it may be of a mixture of components before preparation (a form of powder and the like), those already prepared (a form of liquid and the like) or the like.

A culture medium used in the present invention may contain a reagent commonly used in cell culture. Such reagents include antibiotics (gentamycin, kanamycin and the like), albumin, blood serum (human blood serum, fetal bovine serum and the like), 2-mercaptoethanol, sodium pyruvate, growth factors such as insulin, L-glutamine, transferrin and the like.

A culture medium containing IL-2 and/or IL-15 and anti-CD16 monoclonal antibody can be prepared by the known method of manufacturing a culture medium. For example, it can be prepared by adding IL-2 and/or IL-15 and anti-CD16 monoclonal antibody to the aforementioned medium components. Further, a culture medium containing anti-CD16 monoclonal antibody may also be prepared by adding components other than anti-CD16 monoclonal antibody to a flask where anti-CD16 monoclonal antibody is pre-coated.

There is no particular limitation for the culture conditions in the first step, and conditions used for common cell culture may be used. For example, culturing may be performed at 30 to 38° C. and 5 to 10% CO2. A culture period may be long enough for activating and proliferating mononuclear cells and differentiating them into NK cells, NKT cells and the like, and may be 3 days or more, preferably 5 days. Further, the activity of mononuclear cells, NK cells and the like may be decreased when cultured for a long period of time. Therefore, the culture period may be 14 days or less. However, NK cells, NKT cells and the like may continue to grow even when cultured for 14 days or more. Therefore, a cell count of 5 billion or more can also be obtained by, for example, culturing for 21 days. The activity of cells can be maintained even in a case where cultured for a long period of time (for example, for 21 days) by appropriately replacing culture media by a known method during the culture period.

Second Step (Step of Proliferating T Cells)

The second step in the present invention is performed after the aforementioned first step. In the second step, culture is performed under conditions where mononuclear cells are preferentially differentiated into cytotoxic T cells so that mononuclear cells which were less sufficiently stimulated (or not stimulated) in the first step are allowed to be selectively differentiated into T cells and further allowed to grow. Further, in the second step, NK cells, NKT cells, γδT cells and the like differentiated, activated and also proliferated in the first step are directly or indirectly stimulated by the T cells activated in the second step. As a result, NK cells, NKT cells and γδT cells may also be amplified even though the second step is performed under culture conditions in which T cells are selectively stimulated. Note that the term "conditions in which mononuclear cells are preferentially differentiated into T cells" as used in the present invention refers to a culture condition commonly used to differentiate mononuclear cells into T cells (for example, culturing in the presence of anti-CD3 antibody, culturing in the presence of anti-CD3 antibody and IL-2, culturing in the presence of anti-CD3 antibody, IL-2 and IL-15, culturing in the presence of anti-TCR antibody and the like).

In a case where mononuclear cells are to be differentiated into NK cells after cultured under conditions in which mononuclear cells are preferentially differentiated into cytotoxic T cells (that is, in a case where the second step is performed before the first step), many T cells are amplified, resulting in a decreased proportion of NK cells and the like. Then, only an immune cell-containing composition having an excessive proportion of T cells can be obtained. Therefore, it is difficult to differentiate mononuclear cells into multiple types of immune cells in a well-balanced manner, and also difficult to proliferate these immune cells.

In the second step, medium replacement and the like is performed after the first step, and cells are cultured in a culture medium which can allow differentiation of mononuclear cells into T cells and growth of T cells. As such a culture medium, any known medium which can allow differentiation of mononuclear cells into T cells and growth of T cells can be used. Specifically, a culture medium can be used in which 1 to 100 μg/mL of anti-CD3 antibody (for example, anti-CD3ε monoclonal antibody) is added to a culture medium usable in the first step (a serum-free synthetic medium for lymphocytes and the like).

There is no particular limitation for the culture conditions in the second step, and conditions used for common cell culture may be used. For example, culturing may be performed at 30 to 38° C. and 5 to 10% CO2. A culture period may be long enough to allow mononuclear cells to differentiate into T cells, and may be 48 hours or more, and preferably 3 days. Further, when cultured for a long period of time, T cells may be excessively proliferated, and it may be difficult to obtain an immune cell-containing composition containing NK cells, NKT cells and T cells in a well-balanced manner. Therefore, a culture period may be 7 days or less, preferably 5 days or less, more preferably 3 days or less. Further, medium replacement may be appropriately performed during culture by the conventionally known method.

A third step of performing culturing in a culture medium containing IL-2 and/or IL-15 and anti-CD16 monoclonal antibody may be provided after the second step. This can allow NK cells and the like obtained from the first step to proliferate and the adjustment of the proportions of NK cells, NKT cells and T cells in an immune cell-containing composition. Therefore, an immune cell-containing composition containing multiple types of immune cells in a well-balanced manner can be obtained more efficiently. The conditions in the aforementioned first step can be used as those in the third step.

Immune Cell-Containing Composition Obtained by Manufacturing Method According to Present Invention Unlike the conventional method, an immune cell-containing composition obtained by the manufacturing method according to the present invention contains multiple types of immune cells in a well-balanced manner so that no specific type of cells is excessive in proportion. The phrase "containing multiple types of immune cells in a well-balanced manner" as used in the present invention means that the proportions of each type of immune cell in an immune cell-containing composition are close to the proportion in the living body. However, the proportion of NK cells in an immune cell-containing composition higher than that in the living body can also be considered as a state "containing multiple types of immune cells in a well-balanced manner" in that immunocompetence can be efficiently enhanced. States "containing multiple types of immune cells in a well-balanced manner" include, for example, those containing 40 to 60% of NK cells, 15 to 25% of NKT cells, 2 to 5% of γδT cells, 20 to 30% of T cells and 0.01 to 0.2% of Treg cells in the total number of cells. The proportions of each type of immune cell in an immune cell-containing composition can be determined by flow cytometry. However, the balance of the cells listed above as examples may be appropriately changed by adjusting culture conditions and the like depending on the treatment policy of a patient. Examples of adjustment of culture conditions include increasing the amount of an NKT cell stimulant as compared with that of an NK cell stimulant in a culture medium and the like.

Whether a cell obtained by the manufacturing method according to the present invention is an NK cell and the like or not is to be determined by analyzing a marker on a cell surface of the obtained cell using flow cytometry. For example, an NK cell, a T cell, an NKT cell, a γδT cell and a Treg cell are identified as a CD3+CD56+ cell, a CD3-CD19+ cell, a CD3+CD19-cell, a CD3-CD56+ cell and a CD3+γδTCR+ cell, respectively. Further, a T cell and an NKT cell can be identified with anti-TCR alpha antibody, anti-TCRV alpha24 antibody and the like, respectively.

Further, according to the present invention, a sufficient amount of immune cells (for example, 106 to 108 cells/mL or more) can be obtained from a small amount of blood (for example, 1 to 100 mL, preferably 1 to 50 mL). Therefore, an amount of immune cells required for cellular immunotherapy can be conveniently obtained without imposing burden on the living body. Here, the term "the amount of immune cells" as used in the present invention refers to the total amount (total cell count) of at least NK cells, NKT cells and T cells. Further, according to the present invention, the sufficient amount of immune cells as described above can be obtained in a culture period as short as, for example, the total 14 days of the first step and the second step.

The immune cell-containing composition obtained by the manufacturing method according to the present invention may be used directly for treating a patient, or may be stored by cryopreservation and the like using a conventionally known method. Immune cells (NK cells, NKT cells, T cells and the like) in the immune cell-containing composition obtained by the manufacturing method according to the present invention can maintain an active state even when maintained in physiological saline and the like. The active state of immune cells can be determined by analyzing cell surface markers (CD69 and the like) of the obtained cells using flow cytometry. Further, a composition for treating cancer can be prepared by adding physiological saline, human serum albumin and the like to the immune cell-containing composition obtained by the manufacturing method according to the present invention. The above composition for treating cancer can be administered into a patient as an injectable and the like.

Immune cells (NK cells, NKT cells, T cells and the like) in the immune cell-containing composition obtained by the manufacturing method according to the present invention can be effectively used for cancer treatment and the like because they have cellular cytotoxicity. The cellular cytotoxicity of immune cells can be determined by the 51Cr release method and the like. Further, immune cells in the immune cell-containing composition obtained by the manufacturing method according to the present invention can also produce IFN-γ, which has antitumor activity. IFN-γ can be measured by the known ELISA method and the like.

EXAMPLES

Below, the present invention will be described based on Examples. However, the present invention shall not be limited to the following Examples.

Reference Test 1: Proportions of Each Immune Cell Contained in Blood of Healthy Subjects Using a blood withdrawing device (Product name: "BD Vacutainer CPT cell preparation tube," Becton, Dickinson and Company), 24 mL of blood was withdrawn from each of 6 healthy subjects. Human peripheral blood mononuclear cells (PBMC) were recovered from each blood sample, and human NK cells were obtained from the obtained PBMC.

FIG. 1(A) shows the cell counts of the recovered PBMC for each of the 6 healthy subjects. FIG. 1(B-1) shows a typical cell distribution in the obtained PBMC. FIG. 1(B-2) shows a typical result from the FACS analysis of the obtained PBMC using FITC-labeled anti-CD19 antibody and PE-labeled anti-CD3 antibody. The terms "FSC" and "SSC" in FIG. 1 (B-1) refer to forward scattering (forward scatter) and side scattering (side scatter), respectively.

Further, the proportions of each type of cell in the obtained PBMC are shown in Tables 1 and 2. Note that hereinafter, B cells, T cells, NKT cells, NK cells and γδT cells correspond to CD3-CD19+ cells, CD3+CD19− cells, CD3+CD56+ cells, CD3-CD56+ cells and CD3+γδTCR+ cells, respectively.

Anti-CD3 antibody and anti-CD56 antibody
Anti-CD3 antibody and anti-γδTCR antibody
CD56 antibody and γδTCR antibody
CD4 antibody and CD25 antibody FIG. 2(A) shows patterns of subsets of lymphocytes in the obtained PBMC, and FIG. 2(B) shows patterns of monocytes in the obtained PBMC.

(First Step)

Next, the obtained PBMC was suspended in a 50 mL culture medium (KBM550, Kohjin Bio Co., Ltd.) supplemented with 175 IU/mL of human IL-2 and 25 ng/mL of human IL-15, and cultured for 5 days in a 75 cm2 flask pre-coated with anti-CD16 monoclonal antibody (this step corresponds to the "first step," and the last day of culturing was designated as "Day 5"). Note that a culture medium supplemented with 175 IU/mL of human IL-2 and 25 ng/mL of human IL-15 and allowed to make contact with pre-coated anti-CD16 monoclonal antibody was designated a "NK-cell growth medium." The above NK-cell growth medium contains IL-2, IL-15 and anti-CD16 monoclonal antibody.

(Second Step)

On Day 5, cells were recovered from the flask and suspended in an NK-cell growth medium, and cultured for 2 days in a sterilized gas-permeable cell culture bag (250 mL, Kohjin Bio Co., Ltd.) containing an NK-cell growth medium (150 mL) and pre-coated with anti-CD3ε monoclonal antibody (this step corresponds to the "second step," and the last day of culturing was designated "Day 7"). This cultured material (culture) corresponds to the immune cell-

TABLE 1

| | Total cell count | Cell count per 1 mL | Proportion in PBMC (%) | | | | | |
|---|---|---|---|---|---|---|---|---|
| | ($\times 10^7$) | ($\times 10^6$) | Monocyte | B cell | T cell | NKT cell | NK cell | γδT cell |
| Healthy subject 1-1 | 4.6 | 1.9 | 3.93 | 7.38 | 50.07 | 4.7 | 7.38 | 3.22 |
| Healthy subject 1-2 | 5.3 | 2.2 | 7 | 7.96 | 51.25 | 6.87 | 17.76 | 3.04 |
| Healthy subject 1-3 | 4.9 | 2 | 17.84 | 8.84 | 45.33 | 5.84 | 11.97 | 2.8 |
| Healthy subject 1-4 | 6.1 | 2.5 | 23.89 | 7.8 | 41.3 | 5.72 | 13.65 | 2.37 |
| Healthy subject 1-5 | 5.5 | 2.3 | 9.46 | 9.13 | 41.03 | 5.17 | 12.7 | 2.83 |
| Healthy subject 1-6 | 7.1 | 2.9 | 8.12 | 4.99 | 26.27 | 3.36 | 7.6 | 1.44 |

TABLE 2

| | Total cell count | Cell count per 1 mL | Absolute cell count ($\times 10^7$) | | | | | |
|---|---|---|---|---|---|---|---|---|
| | ($\times 10^7$) | ($\times 10^6$) | Monocyte | B cell | T cell | NKT cell | NK cell | γδT cell |
| Healthy subject 1-1 | 4.6 | 1.9 | 0.18 | 0.34 | 2.3 | 0.22 | 0.34 | 0.15 |
| Healthy subject 1-2 | 5.3 | 2.2 | 0.37 | 0.42 | 2.7 | 0.36 | 0.94 | 0.16 |
| Healthy subject 1-3 | 4.9 | 2 | 0.87 | 0.43 | 2.22 | 0.29 | 0.59 | 0.14 |
| Healthy subject 1-4 | 6.1 | 2.5 | 1.46 | 0.48 | 2.5 | 0.35 | 0.83 | 0.14 |
| Healthy subject 1-5 | 5.5 | 2.3 | 0.52 | 0.5 | 2.25 | 0.28 | 0.7 | 0.16 |
| Healthy subject 1-6 | 7.1 | 2.9 | 0.58 | 0.35 | 1.9 | 0.24 | 0.54 | 0.1 |

Example 1: Manufacture of Immune Cell-Containing Composition—1

(Recovery of PBMC)

A 24 mL blood sample was withdrawn from each of 4 healthy subjects to recover PBMC (this time point is referred to as "Day 0").

Figure 2:
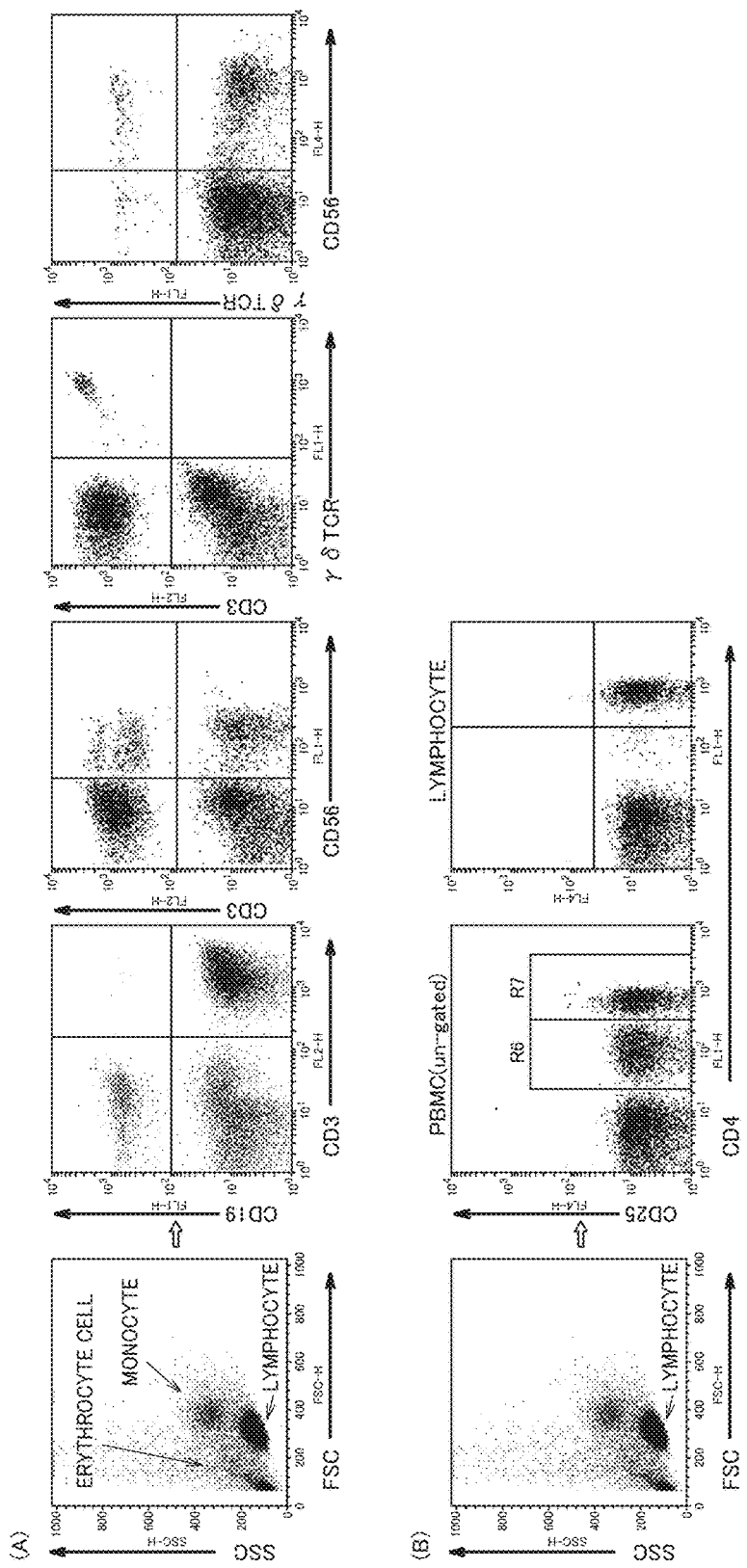
FIG. 2 shows typical results from the FACS analysis of PBMC recovered from a healthy subject.

FIG. 2 shows typical results from the FACS analysis of the obtained PBMC using any of the following combinations of antibodies. Anti-CD3 antibody and anti-CD19 antibody containing composition obtained by the manufacturing method according to the present invention.

(Third Step)

On Day 7, the cell culture bag after culturing was connected to a sterilized gas-permeable cell culture bag (1 L, Kohjin Bio Co., Ltd.) containing an NK-cell growth medium (1000 mL), and further cultured for 7 days under a humid environment at 37° C. and 5% CO2 (this step corresponds to the "third step") to obtain a cultured material (a culture). This cultured material corresponds to the immune cell-containing composition obtained by the manufacturing method according to the present invention.

Figure 3:
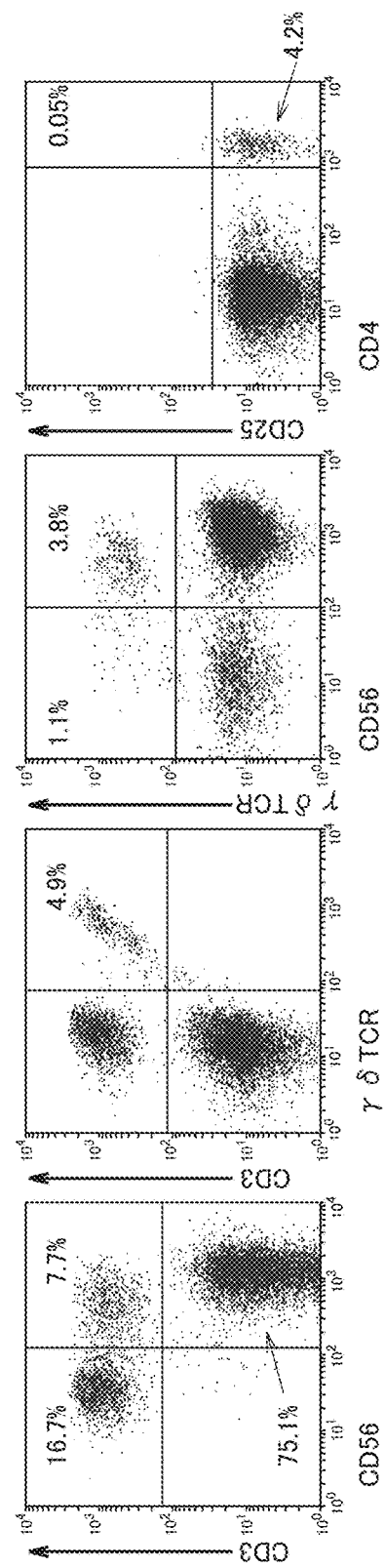
FIG. 3 shows typical results from the FACS analysis of an immune cell-containing composition obtained in an Example of the present invention.

FIG. 3 shows typical results from the FACS analysis of immune cells in the immune cell-containing composition obtained via the above first to third steps. As shown in FIG. 3, the proportions of each type of cell after culturing were as follows: NK cells=75.1%, NKT cells=7.7%, γδT cells=4.9%, T cells=16.7%, CD56 negative γδT cells=1.1%, cytotoxic γδT cells=3.8%, regulatory T cells (Treg)=0.05%, helper T cells=4.2%. That is, according to the present invention, NK cells and the like can be proliferated in a well-balanced manner without having an excessive proportion of T cells.

Example 2: Manufacture of Immune Cell-Containing Composition—2

The "first step" and the "second step" were performed as in Example 1, and the proportions of each type of immune cell before culturing (before the "first step") and after culturing (after the "first step" and the "second step") were studied. Results are shown in Tables 3 to 5.

TABLE 4

| | Proportion in PBMC (%) | | | | | | |
|---|---|---|---|---|---|---|---|
| | Monocyte | B cell | T cell | NKT cell | NK cell | γδT cell | Treg |
| Healthy subject 2-1 (before culturing) | 13.8 | 18.8 | 49.2 | 2.1 | 11.5 | 1.4 | 2.87 |
| Healthy subject 2-1 (after culturing) | 0 | 0 | 16.7 | 7.7 | 75.1 | 4.9 | 0.25 |
| Healthy subject 2-2 (before culturing) | 16.9 | 12.6 | 41.7 | 4.1 | 15 | 2.28 | 0.38 |
| Healthy subject 2-2 (after culturing) | 0 | 0 | 16.8 | 10.2 | 65.2 | 8.26 | 0.15 |
| Healthy subject 2-3 (before culturing) | 11.9 | 12.2 | 51.4 | 2.8 | 14.7 | 1.6 | 0.66 |
| Healthy subject 2-3 (after culturing) | 0 | 0 | 32.4 | 34 | 17.6 | 15.6 | 0.13 |
| Healthy subject 2-4 (before culturing) | 12 | 8.4 | 52.2 | 2 | 19 | 2 | 1.57 |
| Healthy subject 2-4 (after culturing) | 0 | 0 | 19.3 | 4.5 | 71.1 | 3.86 | 0.1 |

TABLE 5

| | Absolute cell count ($\times 10^7$) | | | | | | |
|---|---|---|---|---|---|---|---|
| | Monocyte | B cell | T cell | NKT cell | NK cell | γδT cell | Treg |
| Healthy subject 2-1 (before culturing) | 0.93 | 1.27 | 3.32 | 0.14 | 0.78 | 0.095 | 0.19 |
| Healthy subject 2-1 (after culturing) | 0 | 0 | 44.8 | 20.6 | 201.3 | 13.1 | 0.67 |
| Healthy subject 2-2 (before culturing) | 0.55 | 0.41 | 1.37 | 0.13 | 0.49 | 0.075 | 0.012 |
| Healthy subject 2-2 (after culturing) | 0 | 0 | 41.3 | 25.1 | 160.4 | 20.3 | 0.37 |
| Healthy subject 2-3 (before culturing) | 0.4 | 0.41 | 1.72 | 0.094 | 0.49 | 0.054 | 0.022 |
| Healthy subject 2-3 (after culturing) | 0 | 0 | 155.3 | 162.9 | 84.3 | 74.7 | 0.62 |
| Healthy subject 2-4 (before culturing) | 0.81 | 0.56 | 3.5 | 0.13 | 1.27 | 0.13 | 0.1 |
| Healthy subject 2-4 (after culturing) | 0 | 0 | 66.4 | 15.5 | 244.6 | 13.3 | 0.34 |

TABLE 3

| | Amount of collected blood (mL) | Total cell count ($\times 10^7$) | Cell count per 1 mL ($\times 10^6$) |
|---|---|---|---|
| Healthy subject 2-1 (before culturing) | 24 | 6.75 | 2.8 |
| Healthy subject 2-1 (after culturing) | — | 268 | — |
| Healthy subject 2-2 (before culturing) | 24 | 3.28 | 1.4 |
| Healthy subject 2-2 (after culturing) | — | 246 | — |
| Healthy subject 2-3 (before culturing) | 24 | 3.35 | 1.4 |
| Healthy subject 2-3 (after culturing) | — | 479 | — |
| Healthy subject 2-4 (before culturing) | 24 | 6.71 | 2.8 |
| Healthy subject 2-4 (after culturing) | — | 344 | — |

As shown in Tables 3 to 5, according to the present invention, an immune cell-containing composition containing NK cells and the like in a well-balanced manner can be obtained without having an excessive proportion of T cells.

Example 3: Activity of Immune Cells in Immune Cell-Containing Composition

An immune cell-containing composition obtained as in Example 1 was recovered with a 1 L culture medium (KBM550, Kohjin Bio Co., Ltd.), and re-suspended in 100 mL of pharmaceutical grade physiological saline (Terumo Corp.) supplemented with 0.2% human serum albumin (Nihon Pharmaceutical Co., Ltd.) or a pharmaceutical grade physiological saline alone. Next, the cells were maintained for 24 hours at 4° C., and analyzed by FACS. Typical results are shown in FIG. 4.

FIGS. 4(1) and 4(2) reveal that each type of immune cells in the immune cell-containing composition obtained by the manufacturing method according to the present invention still expressed CD69 even after being maintained for 24 hours in physiological saline. Considering that CD69 is an activation marker of a cell, each type of immune cell in the immune cell-containing composition obtained by the manufacturing method according to the present invention is found to be capable of maintaining an active state. The reduced activity of such immune cells which may occur during transportation can be prevented even in a case where they are transported to distant places and the like after preparation.

Example 4: Manufacture of Immune Cell-Containing Composition—3

The same tests were performed as in Example 2 except that culture media shown in Tables 6 to 8 were used instead of "KBM550." Note that "KBM570," "AIM-V" and "Milteni" are available from Kohjin Bio Co., Ltd., Invitrogen and Miltenyi Biotec K. K., respectively. The proportions and the like of each type of immune cell in the obtained immune cell-containing composition are shown in Tables 6 to 8. Note that in Table 6, "at the start of culturing" means before performing the "first step," and "after culturing" means after performing the "first step" and the "second step."

TABLE 6

| | Type of culture medium | Amount of collected blood (mL) | Cell count at the start of culturing ($\times 10^7$) | Cell count after culturing ($\times 10^7$) |
|---|---|---|---|---|
| Healthy subject 3-1 | KBM570 | 12 | 3.37 | 138 |
| Healthy subject 3-1 | AIM-V | 12 | 2.82 | 47.8 |
| Healthy subject 3-2 | AIM-V | 12 | 2.33 | 70.9 |
| Healthy subject 3-2 | AIM-V | 12 | 1.9 | 92.2 |
| Healthy subject 3-3 | Milteni | 12 | 1.9 | 45.5 |

TABLE 7

| | Proportion in PBMC in immune cell-containing composition (%) | | | | | | |
|---|---|---|---|---|---|---|---|
| | Monocyte | B cell | T cell | NKT cell | NK cell | γδT cell | Treg |
| Healthy subject 3-1 | 0 | 0 | 15.3 | 7.5 | 76.8 | 5.1 | 0.39 |
| Healthy subject 3-1 | 0 | 0 | 10.2 | 8.2 | 80.9 | 6.3 | 0.33 |
| Healthy subject 3-2 | 0 | 0 | 29.8 | 30 | 38.9 | 21.2 | 2.5 |
| Healthy subject 3-2 | 0 | 0 | 21.6 | 12.6 | 64.9 | 7.4 | 0.24 |
| Healthy subject 3-3 | 0 | 0 | 36.3 | 19.1 | 44.1 | 9.2 | 0.47 |

TABLE 8

| | Absolute number of cells in immune cell-containing composition ($\times 10^7$) | | | | | | |
|---|---|---|---|---|---|---|---|
| | Monocyte | B cell | T cell | NKT cell | NK cell | γδT cell | Treg |
| Healthy subject 3-1 | 0 | 0 | 21.1 | 10.4 | 105.9 | 7 | 0.54 |
| Healthy subject 3-1 | 0 | 0 | 4.9 | 3.9 | 38.7 | 3 | 0.16 |
| Healthy subject 3-2 | 0 | 0 | 21.1 | 21.3 | 27.6 | 15 | 1.77 |
| Healthy subject 3-2 | 0 | 0 | 19.9 | 11.6 | 59.8 | 6.8 | 0.22 |
| Healthy subject 3-3 | 0 | 0 | 16.5 | 8.7 | 20 | 4.2 | 0.21 |

Tables 6 to 8 reveal that the present invention can provide an immune cell-containing composition containing NK cells and the like in a well-balanced manner without having an excessive proportion of T cells regardless of the culture media used.

Example 5: Manufacture of Immune Cell-Containing Composition—4

The same tests were performed as is Example 2 except that culture media shown in Tables 9 to 11 and containing either human IL-2 or human IL-15 were used instead of "KBM550." The proportions and the like of each type of immune cell in the obtained immune cell-containing composition are shown in Tables 9 to 11. Note that in the Tables, "at the start of culturing" or "before culturing" means before performing the "first step," and "after culturing" means after performing the "first step" and the "second step."

TABLE 9

| | Type of culture medium | Amount of collected blood (mL) | Cell count at the start of culturing ($\times 10^7$) | Total cell count ($\times 10^7$) | Cell count per 1 mL ($\times 10^6$) |
|---|---|---|---|---|---|
| Before culturing | — | 24 | — | 4.12 | 1.7 |
| After culturing (IL-2) | AIM-V | — | 2 | 160 | — |
| After culturing (IL-15) | AIM-V | — | 2 | 188 | — |

TABLE 10

| | Proportion in PBMC (%) | | | | | | |
|---|---|---|---|---|---|---|---|
| | Monocyte | B cell | T cell | NKT cell | NK cell | γδT cell | Treg |
| Before culturing | 9.45 | 11 | 58.1 | 0.65 | 14.2 | 1.5 | 0.91 |
| After culturing (IL-2) | 0 | 0 | 13.4 | 0.74 | 68.8 | 8.67 | 0.23 |
| After culturing (IL-15) | 0 | 0 | 0.39 | 3.9 | 81.8 | 6 | 0.09 |

TABLE 11

| | Absolute cell count ($\times 10^7$) | | | | | | |
|---|---|---|---|---|---|---|---|
| | Monocyte | B cell | T cell | NKT cell | NK cell | γδT cell | Treg |
| Before culturing | 0.39 | 0.45 | 2.4 | 0.027 | 0.59 | 0.06 | 0.037 |
| After culturing (IL-2) | 0 | 0 | 21.4 | 1.2 | 110 | 13.9 | 0.37 |
| After culturing (IL-15) | 0 | 0 | 0.73 | 7.3 | 154 | 11.3 | 0.16 |

Tables 9 to 11 reveal that the present invention can provide an immune cell-containing composition containing NK cells and the like in a well-balanced manner without having an excessive proportion of T cells even in the presence of either human IL-2 or human IL-15.

Example 6: Measurement of Cellular Cytotoxicity

An immune cell-containing composition was obtained as in Example 2. The obtained immune cell-containing composition was transferred into a 15 mL centrifuge tube, and centrifugation (1400 rpm, 5 minutes) was performed. The supernatant was then removed to obtain cells. The cellular cytotoxicity of the obtained cells was computed by performing the 51Cr release method (the ratio (E:T) of effector cells (the cell count in an immune cell-containing composition) and target cells (the cell count of K562)=20:1) using human erythroblastic leukemia cells (K562). Results are shown in FIG. 5.

Note that cellular cytotoxicity was computed according to the following expression. In the expression, the term "cpm (an abbreviation for counts per minutes)" refers to the number of radiation per minute.

((mean cpm experimental release−mean cpm spontaneous release)/(mean cpm maximal release−mean cpm spontaneous release))×100

Figure 5:
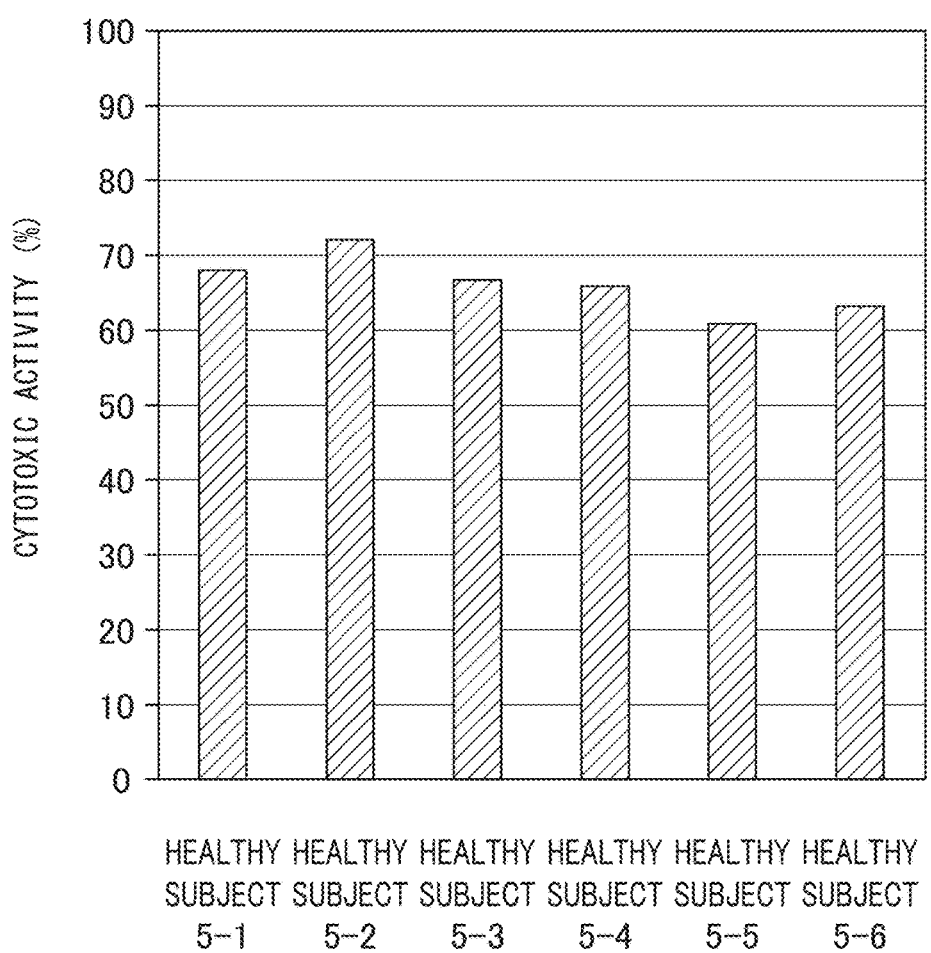
FIG. 5 shows results from measurements of cellular cytotoxicity of an immune cell-containing composition obtained in an Example of the present invention.

FIG. 5 reveals that the present invention can provide immune cells having high cellular cytotoxicity.

Reference Test 2: Studying the Order of the First Step and the Second Step

PBMC was obtained as in Example 1. Next, culturing was performed for 7 days in a 75 cm2 flask pre-coated with 10 μg/mL of anti-CD3 monoclonal antibody and containing 50 mL of a culture medium (KBM550, Kohjin Bio Co., Ltd.) (this step corresponds to the "second step"). Then, culturing was performed for 7 days in a 75 cm2 flask pre-coated with anti-CD16 monoclonal antibody and containing 50 mL of a culture medium (KBM550, Kohjin Bio Co., Ltd.) including IL-2 and IL-15 (this step corresponds to the "first step"). Tables 12 to 14 show results from the FACS analysis of cells before culturing (before the "second step") and after culturing (after the "second step" and the "first step").

TABLE 12

| | Type of culture medium | Amount of collected blood (mL) | Total cell count (×10$^7$) | Cell count per 1 mL (×10$^6$) |
|---|---|---|---|---|
| Before culturing | — | 24 | 4.35 | 1.8 |
| After culturing | KBM550 | — | 385 | — |

TABLE 13

| | Proportion in PBMC in culture (%) | | | | | | |
|---|---|---|---|---|---|---|---|
| | Monocyte | B cell | T cell | NKT cell | NK cell | γδT cell | Treg |
| Before culturing | 15.8 | 8.7 | 48.1 | 3.45 | 15 | 3.35 | 1.12 |
| After culturing | 0 | 0 | 53.7 | 19.5 | 23.4 | 3.97 | 0.16 |

TABLE 14

| | Absolute number of cells after culturing (×10$^7$) | | | | | | |
|---|---|---|---|---|---|---|---|
| | Monocyte | B cell | T cell | NKT cell | NK cell | γδT cell | Treg |
| Before culturing | 6.87 | 3.78 | 20.9 | 0.15 | 0.65 | 0.15 | 0.048 |
| After culturing | 0 | 0 | 206.7 | 75 | 90.1 | 15.3 | 0.6 |

Tables 12 to 14 reveal that the proportion of T cells becomes excessive when a step of culturing in the presence of anti-CD3 monoclonal antibody (that is, the second step) is provided before a step of culturing in the presence of IL-2, IL-15 and anti-CD16 monoclonal antibody (that is, the first step), and an immune cell-containing composition containing NK cells and the like in a well-balanced manner can not be obtained.

The invention claimed is:

1. A method of manufacturing an immune cell-containing composition, the method comprising
    a first step of culturing peripheral blood mononuclear cells (PBMC) in a culture medium containing IL-2, IL-15, and anti-CD16 monoclonal antibody, and
    a second step of performing culturing after the first step under conditions where the PBMC are preferentially differentiated into cytotoxic T cells thereby obtaining the immune-cell containing composition, and wherein culturing in the second step is performed at least in the presence of an anti-CD3 antibody,
    wherein, relative to the PBMC, the immune cell-containing composition comprises an increased percentage of NK cells, an increased percentage of γ§ T cells, and a decreased percentage of T cells, based on the total number of cells in the composition, and the immune cell-containing composition does not comprise B cells.

2. The method of manufacturing an immune cell-containing composition according to claim 1, comprising a third step of performing culturing after the second step in a culture medium containing IL-2 and/or IL-15 and anti-CD16 monoclonal antibody.

3. A method of manufacturing a composition for treating cancer, wherein the composition is manufactured by the manufacturing method according to claim 1.

4. The method of manufacturing an immune cell-containing composition according to claim 1, wherein the second step is any culturing selected from the group consisting of culturing under the presence of anti-CD3 antibody, culturing under the presence of anti-CD3 antibody and IL-2, culturing under the presence of anti-CD3 antibody, IL-2 and IL-15, and culturing under the presence of anti-TCR antibody.

* * * * *